United States Patent
Wang et al.

(10) Patent No.: US 11,351,209 B2
(45) Date of Patent: Jun. 7, 2022

(54) INHIBITORS OF PI3K P-DELTA 110 FOR USE IN DELIVERY OF VIRUSES IN THE TREATMENT OF CANCER

(71) Applicant: Queen Mary University of London, London (GB)

(72) Inventors: Yaohe Wang, London (GB); Mark Ferguson, London (GB); Nicholas R. Lemoine, London (GB)

(73) Assignee: Queen Mary University of London, London (GB)

( * ) Notice: Subject to any disclaimer, the term of this patent is extended or adjusted under 35 U.S.C. 154(b) by 499 days.

(21) Appl. No.: 16/069,101

(22) PCT Filed: Jan. 11, 2017

(86) PCT No.: PCT/GB2017/050051
§ 371 (c)(1),
(2) Date: Jul. 10, 2018

(87) PCT Pub. No.: WO2017/122000
PCT Pub. Date: Jul. 20, 2017

(65) Prior Publication Data
US 2019/0022156 A1  Jan. 24, 2019

Related U.S. Application Data

(60) Provisional application No. 62/277,002, filed on Jan. 11, 2016.

(51) Int. Cl.
| | | |
|---|---|---|
| *A61K 35/76* | (2015.01) | |
| *A61K 45/06* | (2006.01) | |
| *A61K 31/52* | (2006.01) | |
| *A61P 35/00* | (2006.01) | |
| *A61K 9/00* | (2006.01) | |

(52) U.S. Cl.
CPC ............ *A61K 35/76* (2013.01); *A61K 9/0019* (2013.01); *A61K 31/52* (2013.01); *A61K 45/06* (2013.01); *A61P 35/00* (2018.01); *Y02A 50/30* (2018.01)

(58) Field of Classification Search
CPC .................................................... A61K 35/76
See application file for complete search history.

(56) References Cited

U.S. PATENT DOCUMENTS

2012/0100109 A1* 4/2012 Zhang ................. A61K 35/763
  424/93.6
2019/0038713 A1* 2/2019 Sobol .................... A61K 31/00

OTHER PUBLICATIONS

Kenai et al. (Clin Cancer Res; Jun. 1, 2011; 17(11): 3686-3696). (Year: 2011).*
Mark Simon Ferguson (PhD Dissertation. University of London. Aug. 2014. "Enhancement of systemic delivery of oncolytic Vaccinia virus for cancer treatment"). (Year: 2014).*
Hiley et al. (Gene Ther. Feb. 2010 ; 17(2): 281-287. doi:10.1038/gt.2009.132.). (Year: 2010).*
Masako Moriuchi (PhD dissertation. 1998. Howard University. "Effects of bacterial cell wall components on human immunodeficiency virus infection of macrophages"). (Year: 1998).*
Ferguson et al., "Targeting Innate Host Immunity Through PI3K Delta for Enhancement of Systemic Delivery of Oncolytic Vaccinia Virus", Abstracts of the ASGCT 18th annual meeting, 2015, 23(suppl 1), pp. s258-s259.
Forbes et al., "Pharmacological Modulation of Anti-Tumor Immunity Induced by Oncolytic Viruses", Frontiers in Oncology, 2014, 4, pp. 1-12.
Kanai et al., "A Novel Oncolytic Herpes Simplex Virus that Synergizes with Phosphoinositide 3-kinase/Akt Pathway Inhibitors to Target Glioblatoma Stem Cells", Clinical Cancer Research, 2011, 17(11), pp. 3686-3696.
Schirrmacher et al., "Harnessing Oncolytic Virus-Mediated Anti-Tumor Immunity", Frontiers in Oncology, 2014, 4, pp. 1-2.
Tong et al., "PI3K inhibitor LY294002 inhibits activation of the Akt/mTOR pathway induced by the oncolytic adenovirus expressing TRAIL and sensitizes multiple myeloma cells to the oncolytic virus", Oncology Reports, 2014, 31, pp. 1581-1588.
Current Pharmacology, Second Edition, Liu Gengtao, Peking Union Medical College Press, 2008, pp. 274-276.

* cited by examiner

*Primary Examiner* — Scott Long
(74) *Attorney, Agent, or Firm* — Stradley Ronon Stevens & Young LLP (57) ABSTRACT

The present invention provides a composition comprising a phosphatidylinositol 3-kinase (PI3K) inhibitor and a modified virus for separate, subsequent or simultaneous use in the treatment of cancer, wherein the modified virus is for intravenous administration.

6 Claims, 3 Drawing Sheets

INHIBITORS OF PI3K P-DELTA 110 FOR USE IN DELIVERY OF VIRUSES IN THE TREATMENT OF CANCER

CROSS-REFERENCE TO RELATED APPLICATIONS

This application is a 35 U.S.C. § 371 national phase application of PCT Application No. PCT/GB2017/050051, filed Jan. 11, 2017, which claims priority to U.S. Application No. 62/277,002, filed Jan. 11, 2016, each of which is incorporated herein by reference in its entirety.

The present invention relates to an improved method for the delivery of modified viruses to patients, for example in the treatment of cancer.

Modified viruses are viruses that have been selected or engineered for enhanced targeting and killing cancer cells. Modified viruses may include replication competent, conditionally replication competent, replication defective and attenuated viruses. Additionally, modified viruses can also provide the immunostimulatory signals necessary to increase the host's own anticancer response.

Despite advances in minimally invasive surgery, hyper-fractionated radiotherapy and new combinations of chemotherapeutic agents, the survival rates for patients with many solid tumour types have remained unchanged. Modified viruses are attractive therapeutics for treatment of cancers that are resistant to conventional therapies.

Modified viruses are an excellent platform for delivery of immunotherapy as they specifically target tumour cells, leading to firstly a direct lysis and presentation of tumour associated antigens in the context of extra viral danger signals generating a strong immune response. Secondly, they can be engineered to contain transgenes which are expressed within the tumour microenvironment leading to synergistic secondary immune-modulated anti-tumour effects. Recently T-VEC, a genetically engineered HSV-1 virus armed with human GM-CSF, has been licenced by the FDA for the treatment of malignant melanoma by intra-tumoural injection (Andtbacka, et al., J Clin Oncol, 2015. 33(25): p. 2780-8). JX594, another strain of Vaccinia, has been delivered systemically in humans with detectable amounts of transgene expression (Breitbach, C. J., et al., Nature, 2011. 477(7362): p. 99-102) but no strategy has been developed to facilitate effective infection of multiple tumour sites after systemic delivery.

Idelalisib (5-Fluoro-3-phenyl-2-[(1S)-1-(7H-purin-6-ylamino) propyl]-4(3H)-quinazolinone) is a phosphoinositide 3-kinase inhibitor, more specifically, it blocks P110δ, the delta isoform of the enzyme phosphoinositide 3-kinase. It has been through several trials demonstrating minimal toxicities and is used the treatment of chronic lymphocytic leukaemia (Brown et al J Clin Oncol, 2013, supl. Abstract 7003); Furman, et al., N Engl J Med, 2014. 370(11): p. 997-1007); Gopal, et al., N Engl J Med, 2014. 370(11): p. 1008-18.

There is recent published evidence that p110 delta inhibition may have efficacy in not just haemopoietic malignancies but also solid cancers (Ali et al, Nature, 2014. 509 (7505): p. 407-11; Mouchemore et al. FEBS J, 2014. 280 (21): p. 5228-36).

To date, most pre-clinical studies examining systemic delivery of Vaccinia virus have used nude mice bearing xenograft tumours. However, such experimental models are not immunocompetent and it is clear that host immunity is a major barrier to the successful implementation of modified viruses for use in the treatment of cancer. There is therefore a need for improved methods of delivery of such vectors.

The present invention provides a method for enhancing systemic delivery of a modified virus to patients.

According to a first aspect of the invention there is provided a composition comprising a phosphatidylinositol 3-kinase (PI3K) inhibitor and a modified virus for separate, subsequent or simultaneous use in the treatment of cancer, wherein the modified virus is for intravenous administration.

The composition may be especially useful in the treatment of advanced cancer, for example in the treatment of solid tumours in those patients who have failed conventional therapy.

Suitably, the phosphatidylinositol 3-kinase (PI3K) inhibitor is a PI3K delta inhibitor, for example a selective inhibitor of the PI3K catalytic subunit p110δ. In one embodiment the phosphatidylinositol 3-kinase (PI3K) inhibitor has an $IC_{50}$ value of from about 5 nM to about 0.5 µM.

Selective PI3K delta inhibitors are described in WO 2010/0249155 according to Formula 1(S) and Formula 1(R) described therein and WO 2014/072937 according to Formula (I) described therein. WO 2010/0249155 describes the compound IC-87114 (see also Sadhu et al J. Immunology, vol. 170(5):2647-2654, 2003).

The phosphatidylinositol 3-kinase (PI3K) inhibitor may be selected from the group consisting of: IC-87114, PI-103, TGX221, A66, AS 604850, Idelalisib, Wortmannin, Alpelisib, Buparlisib, Copanlisib, Duvelisib, Rigosertib, and Taselisib, or a derivative thereof or a pharmaceutically acceptable salt thereof, as shown in Table 1 below.

TABLE 1

| Name | Structure |
|---|---|
| IC-87114 or 2-[(6-amino-9H-purin-9-yl) methyl]-5-methyl-3-(2-methylphenyl)-4(3H)-quinazolinone or a derivative thereof, or a pharmaceutically acceptable salt thereof: |  |

TABLE 1-continued

| Name | Structure |
|---|---|
| PI-103 or 3-[4-(4-morpholinyl)pyrido[3',2':4,5]furo[3,2-d]pyrimidin-2-yl]-phenol or a derivative thereof, or a pharmaceutically acceptable salt thereof: | |
| TGX221 or 7-methyl-2-(4-morpholinyl)-9-[1-(phenylamino)ethyl]-4H-pyrido[1,2-a]pyrimidin-4-one or a derivative thereof, or a pharmaceutically acceptable salt thereof: | |
| A66 or (2S)-N$^1$-[2-(1,1-Dimethylethyl)-4'-methyl[4,5'-bithiazol]-2'-yl]-1,2-pyrrolidinedicarboxamide or a derivative thereof, or a pharmaceutically acceptable salt thereof: | |
| AS 604850 or 5-[(2,2-difluoro-1,3-benzodioxol-5-yl)methylene]-2,4-thiazolidinedione or a derivative thereof, or a pharmaceutically acceptable salt thereof: | |
| Idelalisib or 5-Fluoro-3-phenyl-2-[(1S)-1-(7H-purin-6-ylamino)propyl]-4(3H)-quinazolinone or a derivative thereof, or a pharmaceutically acceptable salt thereof: | |

TABLE 1-continued

| Name | Structure |
|---|---|
| Wortmannin (a steroid metabolite of the fungi *Penicillium funiculosum* (*Talaromyces wortmannii*) or a derivative thereof, or a pharmaceutically acceptable salt thereof: | |
| PX-866 (a derivative of *Wortmannin*) or (1E,4S,4aR,5R,6aS,9aR)-5-(acetyloxy)-1-[(di-2-propen-1-ylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione or a derivative thereof, or a pharmaceutically acceptable salt thereof: | |
| Alpelisib, or 1,2-Pyrrolidinedicarboxamide, N1-[4-methyl-5-[2-(2,2,2-trifluoro-1,1-dimethylethyl)-4-pyridinyl]-2-thiazolyl]-, (2S)- or a derivative thereof, or a pharmaceutically acceptable salt thereof: | |
| BKM120 (NVP-BKM120, Buparlisib), or 5-(2,6-dimorpholinopyrimidin-4-yl)-4-(trifluoromethyl)pyridin-2-amine or a derivative thereof, or a pharmaceutically acceptable salt thereof: | |

TABLE 1-continued

| Name | Structure |
|---|---|
| BAY 80-6946 (Copanlisib) or 5-Pyrimidinecarboxamide, 2-amino-N-[2,3-dihydro-7-methoxy-8-[3-(4-morpholinyl)propoxy]imidazo[1,2-c]quinazolin-5-yl]-or a derivative thereof, or a pharmaceutically acceptable salt thereof: |  |
| Duvelisib (IPI-145), or 8-chloro-2-phenyl-3-[(1S)-1-(7H-purin-6-ylamino)ethyl]isoquinolin-1-one or a derivative thereof, or a pharmaceutically acceptable salt thereof: |  |
| Rigosertib (ON-01910 sodium salt), or 2-[(2-Methoxy-5-{[(E)-2-(2,4,6-trimethoxyphenyl)ethenesulfonyl]methyl}phenyl)amino] acetic acid or a derivative thereof, or a pharmaceutically acceptable salt thereof: |  |
| Taselisib (GDC-0032), or α,α-dimethyl-4-[5,6-[5,6-2-[3-methyl-1-(1-methylethyl)-1H-1,2,4-triazol-5-yl]imidazo[1,2-d][1,4]benzoxazepin-9-yl]-1H-pyrazole-1-acetamide or a derivative thereof, or a pharmaceutically acceptable salt thereof: |  |

Suitable derivatives of the phosphatidylinositol 3-kinase (PI3K) inhibitors described herein include any substitutions or modifications which do not substantially alter the property of the molecule to be able to act as a phosphatidylinositol 3-kinase (PI3K) inhibitor.

Pharmaceutically acceptable salts of the phosphatidylinositol 3-kinase (PI3K) inhibitor described herein include any suitable salt form formed with an acid such as 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p) or undecylenic acid.

Modified viruses may be a replication competent, conditionally replication competent, replication defective or attenuated virus. The modified virus used in the treatment of cancer can be described therefore as an oncolytic virus.

The modified virus may be a vaccinia virus, a herpes simplex virus, an adenovirus, vesicular stomatitis virus (VSV), measles virus, Newcastle disease virus, a poliovirus, a reovirus, a senecavirus, or an enteric cytopathic human orphan (ECHO) virus, or combinations thereof. The modified virus may be generated by deletion of a certain specific gene or genes (for example by deletion of thymidine kinase), and/or the insertion of a transgene encoding a therapeutic agent.

In one embodiment, the modified virus is a vaccinia virus (VV). Vaccinia virus is a double stranded DNA virus with many features which make it an attractive candidate for modified viral therapy. It shows rapid replication, efficient spread to tumours and strong lytic ability. Additionally, vaccinia has been studied extensively and has a well-defined molecular biology with a large cloning capacity and a variety of commercially available natural and synthetic promoters making it ideal as a vector for carrying heterologous nucleic acid sequences. Vaccinia has well established safety profile and treatments for uncontrolled infections are readily available. Furthermore, vaccinia virus is also able to tolerate hypoxic microenvironment conditions in solid tumours (Hiley et al Gene Ther. 2010, 17:281-287).

The modified vaccinia virus may be selected from the group consisting of the Western Reserve, Wyeth and Lister strains. Suitably, the vaccinia virus is a deletion mutant of one of these strains, for example McCart et al (Cancer Res. 2001, 61; 8751-8757) describe a version of the Western Reserve (WR) strain with deletions in the thymidine kinase (TK) gene and the viral growth factor (VGF) gene and Hung et al (Gene Therapy, 2007, 14; 20-29) describes a TK-deficient vaccinia Lister strain. The modified vaccinia virus may be further modified by the insertion of heterologous genes for example cytokine encoding genes into the virus.

Suitably, the modified vaccinia virus is a deletion mutant where the gene for thymidine kinase is deleted from the viral genome. Such viruses may also be further modified by the insertion of one or more genes encoding a therapeutic agent, for example a cytokine, into the viral genome.

The modified virus may be an adenovirus, for example adenovirus-5, or a herpes simplex virus (HSV), for example HSV-1 or HSV-2. An example of a modified virus which is a HSV-1 virus is the virus construct talimogene laherparepvec ("T-VEC") which is an attenuated form of HSV-1 (strain JS1) which is modified to target cancer cells and to express GM-CSF. Examples of a modified adenovirus include Oncorine™ (H101), Onyx-015™ (Ad2/5 d11520) and enadenotucirev (A11/Ad3 Chimeric Group B adenovirus).

Examples of suitable modified vaccinia viruses for use in accordance with the present invention include but are not limited to viral strains described in WO 2015/150809 (vaccinia virus), WO 2014/063601 (vaccinia virus and adenovirus type 5), JX-594 (thymidine kinase-deleted vaccinia virus with gene encoding GM-CSF). In one embodiment, the modified vaccinia virus is vaccinia virus strain VVL15. Suitably, the vaccinia virus strain is thymidine kinase-deleted and additionally comprises one or more transgenes encoding a therapeutic agent (for example one or more of GM-CSF, IL-12 and/or IL-21), optionally further viral genes in the virus may be deleted or disrupted by gene insertion (gene "knock-out"). For example, the Viral Growth Factor (VGF) and/or NL1 genes may be disrupted or inactivated.

Examples of a therapeutic agent suitable for expression by the modified virus include but are not limited to cytokines, chemokines and growth factors. The cytokine may be an immunomodulating agent such as an interleukin (e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35 and IL-36), an interferon (INF-α, INF-β, INF-γ and INF-w), tumour necrosis factor (TNF) granulocyte macrophage colony-stimulating factor (GM-CSF), or a checkpoint inhibitor PD-1, CTLA-4, TIM-3, LAG-3, BTLA, TIGIT and their respective ligands, for example PD-L1 or PD-L2, CD80 or CD86.

In some embodiments, more than one modified virus may be present in the composition. The composition may therefore comprise at least one modified virus, for example a vaccinia virus and an adenovirus.

The composition may comprise a pharmaceutically acceptable carrier, diluent or excipient.

This aspect of the invention therefore extends to a method of treatment of cancer comprising the step of administering a composition comprising a phosphatidylinositol 3-kinase (PI3K) inhibitor and a modified virus to a subject in need thereof in which the phosphatidylinositol 3-kinase (PI3K) inhibitor and the modified virus are administered separately, subsequently or simultaneously to the subject, wherein the modified virus is administered intravenously.

The invention also therefore provides the use of a phosphatidylinositol 3-kinase (PI3K) inhibitor and a modified virus in the manufacture of a medicament for use in the treatment of cancer, wherein the modified virus is for intravenous administration.

The separate, subsequent or simultaneous administration of the phosphatidylinositol 3-kinase (PI3K) inhibitor and the modified virus for use in the treatment of cancer may be achieved by any convenient route whereby the modified virus for intravenous administration and the PI3K inhibitor is for administration intravenously, intraperitoneally, intramuscularly, orally, intranasally or subcutaneously. In one embodiment, the phosphatidylinositol 3-kinase (PI3K) inhibitor is administered orally and the modified virus is administered intravenously. The phosphatidylinositol 3-kinase (PI3K) inhibitor and the modified virus may be prepared as a combined preparation or may be prepared as separate components.

It is anticipated that the invention may find greatest utility in the treatment of human patients. The subject to be treated may be a mammal, for example a human. The subject may be a rodent for example a rat or a mouse, or a companion animal, for example a cat or a dog. The subject may be a species of agricultural importance, for example an ungulate species, i.e. equine, bovine, porcine, caprine or ovine.

Intravenous delivery may be advantageous in that it should enable simultaneous treatment of primary tumours and any metastatic deposits of cancer cells.

The compositions of the invention may be used in the treatment of cancer, for example in the treatment of a sarcoma, a carcinoma or a lymphoma. Examples of types of cancer which may be treated by the compositions of the invention include but are not limited to lung cancer, liver cancer, breast cancer, bladder cancer, colon cancer, rectal cancer, pancreatic cancer, skin cancer (melanoma, basal cell carcinoma or squamous cell carcinoma), stomach cancer, prostate cancer, bone cancer, adenocarcinoma, osteosarcoma, ovarian cancer, uterine cancer, testicular cancer, neuroendocrine cancer, endocrine cancer, thymus cancer, thyroid cancer, renal cancer, head and neck cancer, esophageal cancer, a peripheral central nervous system cancer or brain cancer. References to a particular cancer include reference to a tumour formed from cancerous cells of the respective tissue or organ.

The tumour may be non-resectable prior to treatment and resectable after treatment. The tumour can be a recurrent, primary, metastatic, and/or multi-drug resistant tumour. The tumour may be a non-malignant tumour/hyperplasia.

A therapeutically effective amount is the dose sufficient to induce tumour lysis (i.e. sufficient to induce (allow survival of) a therapeutically efficacious dose of modified virus). Doses for delivery and administration can be based upon current existing protocols, empirically determined, using animal disease models or optionally in human clinical trials. Initial study doses can be based upon animal studies set forth herein, for a mouse, for example. Doses can vary and depend upon whether the treatment is prophylactic or therapeutic, the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

In an embodiment of the invention, the method further comprises administering to the subject an additional cancer therapy. Cancer therapy as used herein refers to refers to treatment of cancer by any medical or physical means. The additional cancer therapy can be chemotherapy, biological therapy, radiotherapy, immunotherapy, hormone therapy, anti-vascular therapy, cryotherapy, toxin therapy and/or surgery, including combinations thereof. The composition of the invention may therefore comprise one or more anticancer agents or cytostatic drugs.

Methods and uses of the invention as disclosed herein can be practiced immediately or days, months or years after a subject has been identified as having the disease targeted for treatment.

The methods include administering the virus at different schedules. A single dose of the virus may be administered to a subject or a tumour over a 1, 2, 5, 10, 15, 20, or 24 hour period. The virus may be administered over 1, 2, 3, 4, 5, 6, 7 or more days or weeks. The interval between injections can be 1, 2, 3, 4, 5, 6, 7 days or weeks. Typically, multiple doses are administered to the same general target region, such as in the proximity of a tumour or in the case of intravenous administration a particular entry point in the blood stream or lymphatic system of a subject. The vaccinia virus vector may be administered 1, 2, 3, 4, 5, or more times. The vaccinia virus vector could be given before resection of tumours at different schedule and doses.

The methods include administering the virus at different viral concentrations. In certain aspects, the subject is administered at least $5 \times 10^7$, $1 \times 10^8$, $2 \times 10^8$, $5 \times 10^8$, $1 \times 10^9$, $2 \times 10^9$, $5 \times 10^9$, $1 \times 10^{10}$, $5 \times 10^{10}$, $1 \times 10^{11}$, $5 \times 10^{11}$, $1 \times 10^{12}$ or more viral particles or plaque forming units (pfu), including the various values and ranges there between. The viral dose can be administered in 0.1 mL, 1 mL, 2 mL, 3 mL, 4 mL, 5 mL, 6 mL, 7 mL, 8 mL, 9 mL, 10 mL or more, including all values and ranges there between. The dose may be spread over time or by separate injection.

The compositions and methods disclosed in the present invention may be used in different types of gene therapy for example tumour suppressor gene therapy, suicide gene therapy, viral vector immunisation strategies, anti-angiogenic therapy, pro-apoptosis gene therapy and gene replacement therapy. "Oncolytic Viruses for Cancer Therapy: Overcoming the Obstacles" (Wong et al. Viruses 2010, 2, 78-106) is incorporated herein by reference in its entirety.

The compositions and methods disclosed in the present invention may be used in combination with additional therapeutic means or methods in the treatment of cancer, for example surgery, chemotherapy, radiation therapy, molecular cancer therapy or a further gene therapy, which may be used for administering genes that are different from the herein described nucleic acids of the invention.

According to a second aspect of the invention there is provided a kit comprising a phosphatidylinositol 3-kinase (PI3K) inhibitor and a modified virus for use in the treatment of cancer, suitably also comprising instructions for use.

Preferred features of the second and subsequent aspects of the invention are as for the first aspect mutatis mutandis.

The invention will now be further described by way of reference to the following examples and drawings in which:

FIG. 1A shows systemic viral infection significantly increases p110 delta isoform RNA levels in the splenocytes of immunocompetent mice. Either wild-type or nude BALB/c mice were injected with $1 \times 10^6$ CT26 cells in their right flanks before either one intravenous injection of $1 \times 10^8$ PFU VVL15 or PBS. Three mice in each group (Nude/PBS, Nude/VVL15, Immunocompetent/PBS and Immunocompetent/VVL15) were killed immediately after the tail vein injection or three hours later. The amount of p110 delta RNA in the spleens was quantified by qPCR. There is significantly more p110 delta RNA at three hours in the immunocompetent mice treated with VVL15 compared to all other conditions ($P<0.001$).

FIG. 1B shows expression of p110 delta protein is increased by viral infection Bone marrow derived macrophages pooled from two wildtype BALB/c mice were pretreated with either IC87114 at 75 mg kg$^{-1}$ or vehicle buffer for 2 hours before being infected with VVL15 at MOI 5 or mock for 1 hour. p110 delta protein expression was assessed by western blot. Viral infection alone increases the amount of p110 delta protein detected whereas addition of the IC87114 alone or in conjunction with VVL15 does not appear to alter the amount of p110 delta protein detected.

FIG. 1C shows selective inhibition of p110 delta reduces attachment of VVL15 to macrophages. In 2 separate experiments, bone marrow derived macrophages pooled from two wildtype (WT) BALB/c mice were pretreated for 2 hours with IC87114, a selective p110 delta inhibitor, or vehicle buffer. Then a viral attachment assay was undertaken. Subsequently, in the first experiment confocal microscopy was performed after cells were stained with DAPI (blue) and tubulin (green), Vaccinia virus is stained red (Vaccinia virus coat protein antibody). There is less Vaccinia virus detected in the IC87114 treated group. The second experiment quantified the amount of VVL15 present by qPCR. The inhibitor treated group was statistically significantly different from untreated macrophages (P<0.001).

FIG. 1D shows IC87114 affects viral attachment in p110 delta dependent manner. Bone marrow derived macrophages pooled from either two wildtype BALB/c mice or four transgenic mice with p110 delta knocked in (heterozygous knock in [n=2], homozygous knock in [n=2]) were cultured ex vivo and then a viral attachment assay was performed on the transgenic macrophages whereas the wild-type macrophages were pretreated for 2 hours with IC87114 or vehicle buffer and then subsequently a viral attachment assay was undertaken. Both heterozygote and homozygote delta knock in transgenic murine macrophages demonstrated a similar reduction in viral attachment to wild-type macrophages treated with IC87114, all groups were statistically significant from untreated wild-type macrophages (P<0.05 or P<0.01).

FIG. 2A shows pre-treatment with IC87114 before systemic Vaccinia virus injection enhances the tumour luminescence signal in BALB/c mice bearing CT26 flank tumours. Eleven BALB/c mice bearing CT26 flank tumours received either 75 mg kg$^{-1}$ IC87714 or vehicle buffer three hours before one intravenous injection of $1\times10^8$ PFU VVL15. Biodistribution of VVL15 was ascertained by IVIS. There was significantly more signal detected from the group pretreated with 75 mg kg$^{-1}$ IC87114 at days 1, 3, 4 and 5 (P<0.01 at day 1 and P<0.05 at days 3, 4, & 5). These are the combined results of three experiments.

FIG. 2B & FIG. 2C show treatment with oral IC87114 and intra-venous Vaccinia virus significantly reduces the tumour burden and improves survival in BALB/c mice bearing orthotopic 4T1 tumours or CT26 flank tumours.

FIG. 2B shows BALB/c mice bearing CT26 tumours. Forty mice were subcutaneously injected in their shaved right flank with $1\times10^6$ CT26 tumour cells. Mice were pre-treated with either vehicle buffer (Groups A & C) or IC87114 at 50 mg kg$^{-1}$ (Groups B & D) by oral gavage three hours before receiving either an intravenous injection of $1\times10^8$ PFU VVL15 (Groups A & D) or PBS (Groups B & C). This treatment was commenced on day 8 post tumour implantation and repeated on days 11 and 13. There is significantly less tumour burden in the group pre-treated with IC87114 compared to all other groups. Specifically, Group D compared to Group A at days 11 & 13 (P<0.001). Group D compared to Group B at days 11 & 13 (P<0.001). Group D compared to Group C at day 11 (P<0.001). Survival analysis; data are represented in a Kaplan-Meier plot. Mice pre-treated with IC87114 (Group D) survived significantly longer than all the other groups. Specifically, Group D compared to Group A (P<0.01). Group D compared to Group B (P<0.01). Group D compared to Group C (P<0.05).

FIG. 2C shows BALB/c mice bearing orthotopic 4T1 tumours. Thirty-six BALB/c female mice had $1\times10^5$ 4 T1 cells in 50 μl PBS injected orthotopically into the left lower thoracic mammary gland. Mice were pre-treated with either vehicle buffer (Groups A & C) or IC87114 at 75 mg kg$^{-1}$ (Groups B & D) by oral gavage three hours before receiving either an intravenous injection of $1\times10^8$ PFU VVL15 (Groups A & D) or PBS (Groups B & C). This treatment was performed on days 12, 15, and 17 after tumour implantation. There is significantly less tumour burden in the group pre-treated with IC87114 compared to all other groups. Specifically, Group D compared to Group A at days 16 & 19 (P<0.05 & P<0.001 respectively). Group D compared to Group B at day 16 & 19 (P<0.001). Group D compared to Group C at days 16, 19, & 21 (P<0.001). Survival analysis; data are represented in a Kaplan-Meier plot. Mice pre-treated with IC87114 (Group D) survived significantly longer than all other groups. Specifically, Group D compared to Group A (P<0.05). Group D compared to Group B (P<0.01). Group D compared to Group C (P<0.01).

FIG. 2D shows pre-treatment with IC87114 reduces the localisation of Vaccinia virus to the spleen after systemically delivered VVL15 in vivo.

FIG. 2D(i) & FIG. 2D(ii) show photomicrographs of haematoxylin-stained spleen cross sections with immunohistochemical staining for Vaccinia viral coat protein. Arrows mark the virally infected cells: (i) Pre-treated with vehicle buffer; and (ii) Pre-treated with IC87114. FIG. 2D(iii) shows semi-quantification of strongly staining cells in randomly selected high-power fields of ×200 magnification. The number of cells immunoreactive for Vaccinia coat protein were manually counted in each random ×200 magnification field. There is a statistically significant difference between the groups (P<0.001).

FIG. 2E shows IC87114 attenuates anti-viral immunity but has no effect on anti-tumour immunity. Interferon gamma assay on splenocytes derived from BALB/c mice bearing CT26 tumours. Fifteen mice were subcutaneously injected in their shaved right flank with $1\times10^6$ CT26 tumour cells. Mice were pre-treated with either vehicle buffer (Groups A & C) or IC87114 at 75 mg kg$^{-1}$ (Groups B & D) by oral gavage three hours before receiving either an intravenous injection of $1\times10^8$ PFU VVL15 (Groups A & D) or PBS (Groups B & C). An interferon (IFN) gamma ELISA was performed. Anti-tumour immunity: splenocytes were stimulated with mitomycin treated CT26 cells, there was no statistically significant difference between any of the groups. Anti-viral immunity: splenocytes were stimulated with B8R protein, there was more IFN gamma detected in Group A (No Inhibitor+VVL15) compared to all other groups (P<0.05).

The examples are present for the purposes of illustration only and are not to be construed as being limitations on the invention.

Methods

Cell Lines

All cell lines were cultured in Dulbecco's modified Eagle's medium (DMEM) with 5-10% fetal calf serum (FCS) except macrophages which were cultured in Roswell Park Memorial Institute medium (RPMI) with 10% FCS, 28.6 μM Beta Mercaptoethanol (βMCE) and 1% streptomycin/penicillin. The murine colorectal carcinoma cell lines CMT93 and CT26, and breast cancer cell line 4T1 were all obtained from the Cancer Research UK cell bank. The African Green Monkey normal kidney cell line, CV1, was obtained from the American Type Culture Collection (ATCC, VA, USA). Bone marrow-derived macrophages from p110 delta knock-in mice were the kind gift of Professor Vanhaesebroeck (University College London, UK). Cell lines were routinely tested for *Mycoplasma* and were maintained at 37° C. with 5% $CO_2$ unless otherwise stated. Similar passage numbers were used for all experiments. For long term storage, cells were pelleted by centrifugation, and the cell pellet resuspended in DMEM containing 10% dimethyl sulphoxide (DMSO) and 10% FBS. After overnight storage at −80° C. cells were transferred to liquid nitrogen.

Reagents

Merck supplied PI-103 (a PI3 kinase alpha isoform inhibitor) and TGX221 (a PI3 kinase beta isoform inhibitor) as well as the pan-class 1 inhibitor Wortmannin. Tocris Bioscience supplied the Rac1 inhibitor NSC23766, cytochalasin D (an inhibitor of actin polymerisation), Y-27632 (a Rhoassociated protein kinase inhibitor), and nocodazole (an inhibitor of polymerisation of microtubules). Santa Cruz Biotechnology supplied the class 1a selective PI3 kinase alpha inhibitor A66. Sigma-Aldrich supplied AS 604850, a selective class 1 b PI3 kinase gamma isoform inhibitor. Initially Symansis supplied IC87114, the selective class 1a p110 delta isoform inhibitor then subsequently, from March 2012, it was obtained instead from Synkinase. The concentrations used were PI-103 at 80 nM, TGX221 at 0.1 µM, Wortmannin at 0.5 µM, NSC23766 at 50 µM, A66 at 0.5 µM, Cytochalasin D at 10 µM, Y-27632 at 10 µM, Nocodazole at 10 µM and AS 604850 at 1 µM. IC87114 was used at 1 µM concentration for all in vitro assays unless otherwise stated. The Western Blot antibodies were anti-p110δ from Santa Cruz Biotechnologies (sc-7176), and anti-vinculin (V9131) and anti-actin (SAB2500963) from Sigma-Aldrich. The Vaccinia virus antibody used for the immunohistochemical experiments was a rabbit anti-Vaccinia virus polyclonal antibody supplied by AbD Serotec, batch number 250906, and it was used diluted 1:400. MACs buffer was phosphate-buffered saline Dulbecco+2 mM EDTA+0.1% Bovine Serum Albumin (BSA). Pronase was supplied by Roche Applied Science (Cat. No. 10165921001) and dissolved in phosphate-buffered saline (PBS) at 1 mg ml$^{-1}$. MTS (3-(4, 5-dimethylthiazol-2-yl)-5-(3-carboxymethoxyphenyl)-2-(4-sulfophenyl)-2H-tetrazolium) and PMS (phenazine methosulfate) were provided by Promega. T cell culture media (TCM) was RPMI-1640, 10% FCS, 1% streptomycin, 1% penicillin, and 1% sodium pyruvate. In vivo IC87114 was used at 75 mg kg$^{-1}$ by oral gavage. Recombinant mouse macrophage colony stimulating factor (M-CSF) was supplied by R&D Systems, catalog no. 415-ML. It was used at a concentration of 30 ng ml$^{-1}$. D-Luciferin was supplied by Caliper Life Sciences (Lot Number: 124358465) and used at 15 mg ml$^{-1}$. Vehicle buffer, used as either a control or to dissolve IC87114, was made by the addition of 0.25% Tween-20 and 0.5% carboxymethylcellulose to PBS.

Virus

VVL15 was the kind gift of Professor Istvan Fodor (Loma Linda University Campus, Loma Linda, Calif., USA). It was constructed by the insertion of the firefly luciferase and the lacZ reporter genes into the thymidine kinase region of VVLister under the control of the early-late vaccinia p7.5 promoter.

EXAMPLE 1: INFECTION OF TUMOUR CELLS BY A MODIFIED VIRUS IN NUDE MICE AND IMMUNOCOMPETENT MOUSE MODELS

Figure 1:
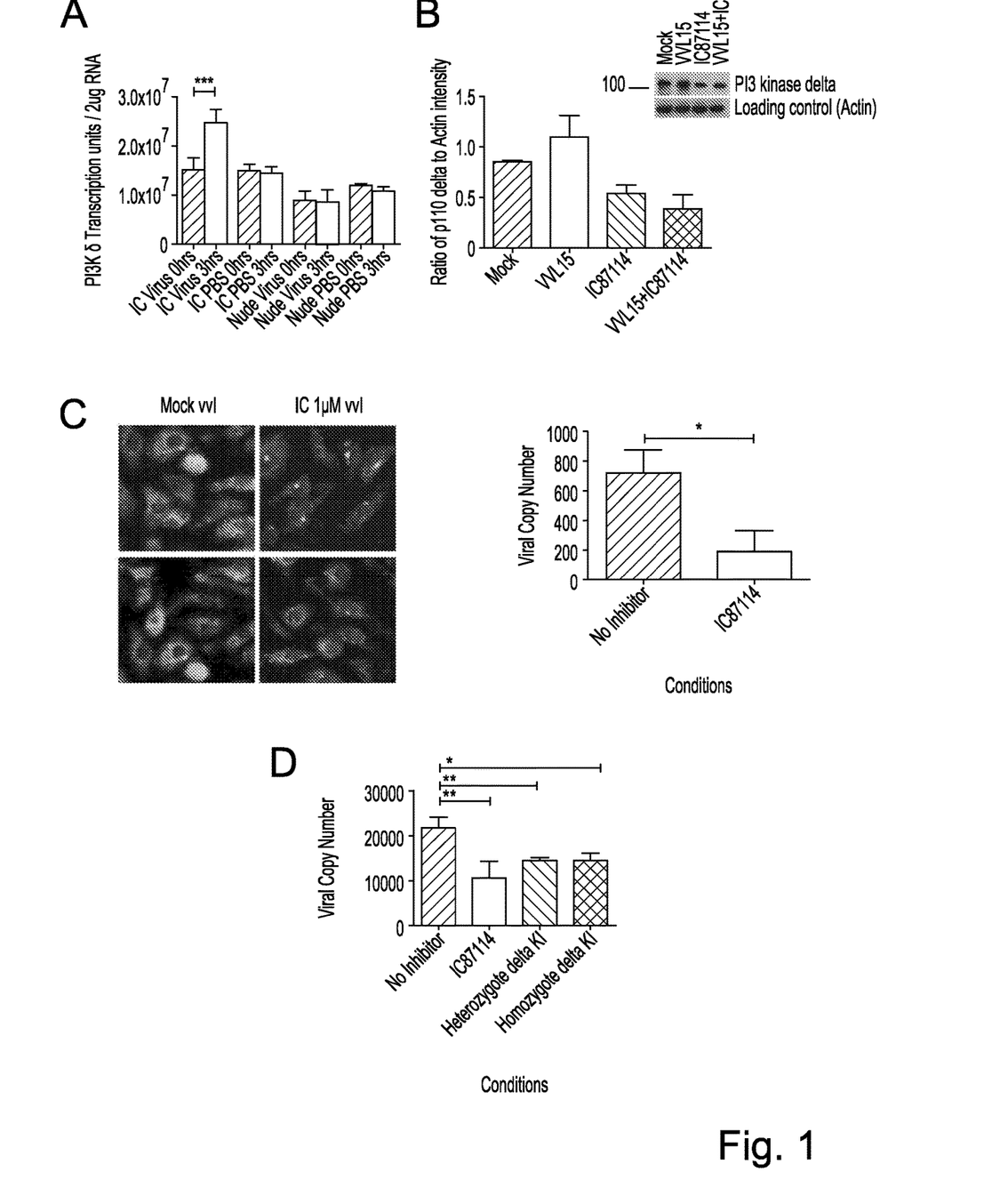

FIG. 1A shows there is significantly more p110 delta RNA at three hours in the splenocytes of immunocompetent mice treated with VVL15 compared to all other conditions (P<0.001). This implies that there is a virally induced up-regulation of p110 delta RNA in splenocytes derived from immunocompetent mice but not nude, providing further clues as to the differences between the models and at least plausibly lending greater weight to the concept that splenic macrophages play a central role in VVL15 clearance. FIG. 1B demonstrates that this up-regulation of p110 delta RNA is translated into protein expression in virally treated immunocompetent mouse macrophages compared to mock-treated. FIG. 1C shows that inhibition of p110 delta by IC87114 (a selective inhibitor) significantly reduces VVL15 attachment to macrophages.

Although IC87114 is thought to be quite specific, it certainly could hamper other kinases (Camps et al., Nat Med, 2005. 11(9): p. 936-43). Therefore there is a need to ascertain that the reduction in VVL15 attachment observed is in fact due to IC87114 blocking p110 delta activity. Accordingly, bone marrow-derived macrophages from transgenic p110 delta knock-in (this is a 'kinase-dead' inactivating mutation) were used in an attachment assay. FIG. 1D shows that there is a similar significant reduction of VVL15 attachment to wild-type macrophages treated with IC87114 compared with both heterozygote and homozygote transgenic macrophages (P<0.01 or P<0.05 respectively). These data suggests that the reduction in attachment seen in wild-type macrophages treated with IC87114 is due to selective p110 delta inhibition. Therefore it is logical to suggest that p110 delta is involved in the process of virus binding to the macrophage. Interestingly, there is no difference in the reduction in attachment between the heterozygote and homozygote p110 delta knock-in macrophages, implying that after a certain level of delta blockade VVL15 attaches to the cell in a p110 delta-independent manner.

Figure 2:
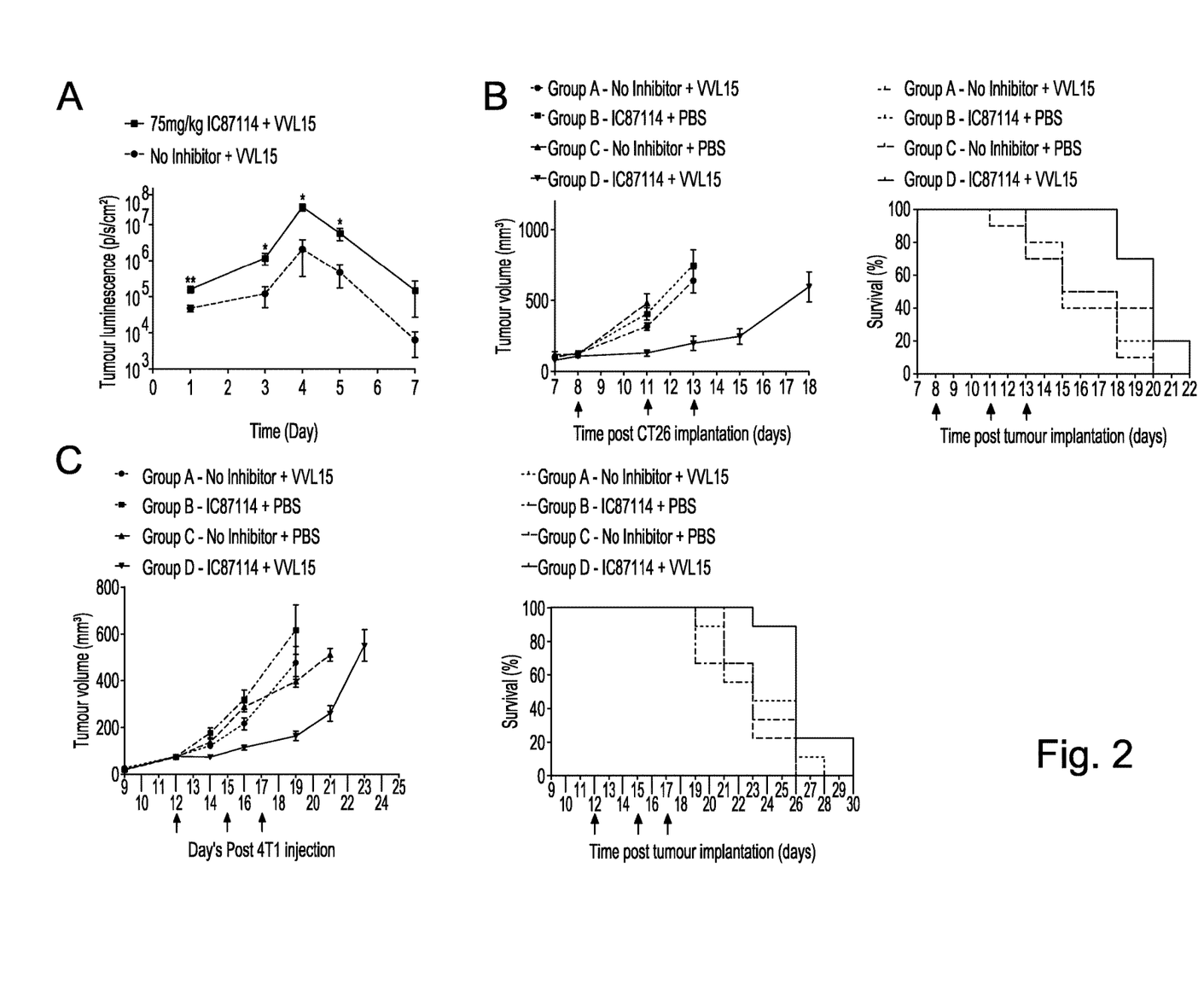

In the present examples, it was decided to use 75 mg kg$^{-1}$ as the dose of IC87714. It was decided to administer this dose three hours prior to VVL15 systemic delivery. This timing was based on the in vitro data shown in FIG. 1C that showed that there was a reduction in viral attachment to macrophages after three hours of incubation with IC87114 and a pharmacokinetics study performed in Rats demonstrating that the time to maximum plasma concentration after oral administration of IC87114 was 4 hours. FIG. 2A shows that the 75 mg kg$^{-1}$ dosing produces consistently higher tumour luminescence compared to control. IC87714 was administered orally followed by intravenous injection of VVL15.

EXAMPLE 2: EFFICACY STUDIES

Subsequently, this combination of inhibitor and virus was used in two efficacy studies in different murine models (FIGS. 2B & 2C) one of which had been optimised as a reliable orthotopic metastatic model mirroring the likely clinical application of this treatment. These studies demonstrated that IC87114 enhances the anti-tumour efficacy of systemically delivered VVL15 in vivo conferring both reduced tumour burden and survival advantage. The tumours in the mice of Group D (IC87114+VVL15, FIGS. 2B & 2C) did eventually start to increase in size and the mice died but VVL15 is a thymidine kinase-deleted virus and is far less efficacious than other available modified Vaccinia viruses armed with immune modulating transgenes.

FIG. 2E illustrates an ex vivo interferon gamma assay performed on splenocytes derived from BALB/c mice bearing CT26 tumours. This demonstrated that splenocytes derived from the mice treated with the optimised regime developed similar anti-tumour IFN gamma responses to all the other groups tested. However, the splenocytes derived from the IC87114+VVL15 group did have reduced levels of IFN gamma after stimulation with the viral protein B8R when compared to splenocytes from the group treated with virus alone. Thus pre-treatment with IC87114 appears to reduce in magnitude the subsequent development of an anti-viral response. This potentially could mean that aside from the effect IC87114 has on macrophages at an early time point it has a separate more lasting effect that leads to reduced anti-viral immunity and to the establishment of an effective infection of the tumours leading to the observed improvement in efficacy compared to virus alone.

The invention claimed is:

1. A method of treating cancer in a subject in need thereof comprising the steps of:
    administering a composition comprising a phosphatidylinositol 3-kinase (PI3K) inhibitor; and subsequently:
    administering a composition comprising a TK-deficient vaccinia virus, in which the TK-deficient vaccinia virus is administered intravenously.

2. The method of claim 1, wherein the phosphatidylinositol 3-kinase delta (PI3K delta) inhibitor is selected from the group consisting of: IC-87114, PI-103, TGX221, A66, AS 604850, Idelalisib, Wortmannin, Alpelisib, Buparlisib, Copanlisib, Duvelisib, Rigosertib, and Taselisib, or a derivative thereof or a pharmaceutically acceptable salt thereof.

3. The method of claim 1, wherein the TK-deficient vaccinia virus is modified by the insertion of a gene encoding a therapeutic agent, or the deletion, or inactivation by insertion, of a viral gene.

4. The method of claim 1, wherein the cancer is selected from the group consisting of lung cancer, liver cancer, breast cancer, bladder cancer, colon cancer, rectal cancer, pancreatic cancer, skin cancer, stomach cancer, prostate cancer, bone cancer, adenocarcinoma, osteosarcoma, ovarian cancer, uterine cancer, testicular cancer, neuroendocrine cancer, endocrine cancer, thymus cancer, thyroid cancer, renal cancer, head and neck cancer, esophageal cancer, a peripheral central nervous system cancer or brain cancer.

5. The method of claim 1, wherein the method further comprises administering an additional anti-cancer agent or cytostatic drug.

6. The method of claim 4, wherein the skin cancer is melanoma, basal cell carcinoma, or squamous cell carcinoma.

* * * * *